US006425890B1

United States Patent
Samuelsson et al.

(10) Patent No.: US 6,425,890 B1
(45) Date of Patent: *Jul. 30, 2002

(54) ABSORBENT ARTICLE WITH A RAISED PORTION

(75) Inventors: Ann Samuelsson, Lindome; Annelie Johansson, Göteborg; Camilla Björklund; Solgun Drevik, both of Mölnlycke; Urban Widlund, Pixbo, all of (SE)

(73) Assignee: SCA Hygiene Products AB, Gothenburg (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/297,746

(22) PCT Filed: Nov. 11, 1997

(86) PCT No.: PCT/SE97/01886
§ 371 (c)(1),
(2), (4) Date: Sep. 1, 1999

(87) PCT Pub. No.: WO98/22062
PCT Pub. Date: May 28, 1998

(30) Foreign Application Priority Data

Nov. 15, 1996 (SE) .............................. 9604221

(51) Int. Cl.⁷ ................................. A61F 13/15
(52) U.S. Cl. .............. 604/385.17; 604/378; 604/385.24
(58) Field of Search ........................ 604/385.01, 347, 604/354, 386, 387, 378, 109, 49.4, 385.08, 385.21, 385.22, 385.23, 385.24, 385.17; 2/49.4, 109

(56) References Cited

U.S. PATENT DOCUMENTS

| 810,119 A | * | 1/1906 | Green ........................ 604/378 |
| 810,120 A | * | 1/1906 | Green ........................ 604/378 |
| 810,131 A | * | 1/1906 | Green ........................ 604/378 |

(List continued on next page.)

FOREIGN PATENT DOCUMENTS

| EP | 0 067 377 A2 * 12/1982 |
| EP | 0 155 515 A1 *  9/1985 |
| EP | 0 155 515 B1 *  9/1985 |

(List continued on next page.)

OTHER PUBLICATIONS http://www.oikos.com/esb/51/wheatboard.html; Iris Communications, Inc.; Jun. 1997.*
http://www.iswonline.com/wwp/199911/isobord.html; Industrial Strength Woosworking; Nov. 1999.*

(List continued on next page.)

*Primary Examiner*—John G. Weiss
*Assistant Examiner*—Phil Bogart
(74) *Attorney, Agent, or Firm*—Burns, Doane, Swecker & Mathis, L.L.P.

(57) ABSTRACT

The invention relates to an absorbent article intended for female users, such as a sanitary napkin, or an incontinence guard, having such a shape and size that it may be substantially accommodated in the crotch region of a pair of panties and having a longitudinal direction, a transverse direction and a thickness direction. The article exhibits a liquid-pervious cover layer and a liquid-impervious cover layer and further an absorbent core consisting of at least one absorbent body, arranged between the two surfaces, and wherein a hump is arranged at the liquid-pervious cover layer of the article. The invention is characterized in that the hump is substantially shape permanent in the transverse direction of the article, both in a wet and in a dry state, and to such an extent that the hump (16) is not deformed in the transverse direction, either temporarily or permanently, by the forces acting on the hump during use of the article.

20 Claims, 4 Drawing Sheets

U.S. PATENT DOCUMENTS

| | | | | |
|---|---|---|---|---|
| 1,946,626 | A * | 2/1934 | Jurgenson | |
| 2,551,663 | A * | 5/1951 | Fox | 128/290 |
| 3,407,814 | A * | 10/1968 | George et al. | 128/290 |
| 3,468,311 | A * | 9/1969 | Gallagher | 128/296 |
| 3,570,493 | A * | 3/1971 | Olsson | |
| 3,888,255 | A * | 6/1975 | Shah et al. | |
| 4,041,950 | A * | 8/1977 | Jones, Sr. | 128/287 |
| 4,047,531 | A * | 9/1977 | Karami | |
| 4,195,634 | A * | 4/1980 | DiSalvo et al. | 128/290 |
| 4,217,901 | A * | 8/1980 | Bradstreet et al. | 128/290 |
| 4,351,340 | A * | 9/1982 | McLeod | |
| 4,386,932 | A * | 6/1983 | Pitts | 640/383 |
| 4,536,181 | A * | 8/1985 | Cook | |
| 4,643,726 | A * | 2/1987 | Gegelys | |
| 4,673,403 | A * | 6/1987 | Lassen et al. | 604/385 |
| 4,804,380 | A * | 2/1989 | Lassen et al. | 604/385.1 |
| 4,828,555 | A * | 5/1989 | Hermansson | |
| 4,846,824 | A * | 7/1989 | Lassen et al. | 604/385.1 |
| 4,865,597 | A * | 9/1989 | Mason, Jr. et al. | 604/385.1 |
| 4,897,084 | A * | 1/1990 | Ternström et al. | |
| 4,911,701 | A * | 3/1990 | Mavinkurve | |
| 5,032,121 | A * | 7/1991 | Mokry | |
| 5,074,855 | A * | 12/1991 | Rosenbluth et al. | 604/385.1 |
| 5,074,856 | A * | 12/1991 | Coe et al. | |
| 5,080,658 | A * | 1/1992 | Igaue et al. | |
| 5,098,422 | A * | 3/1992 | Davis et al. | |
| 5,114,419 | A * | 5/1992 | Daniel et al. | |
| 5,129,893 | A * | 7/1992 | Thoren | 604/385.2 |
| 5,171,302 | A * | 12/1992 | Buell | 604/385.1 |
| 5,181,563 | A * | 1/1993 | Amaral | |
| 5,197,959 | A * | 3/1993 | Buell | 604/385.1 |
| 5,295,987 | A * | 3/1994 | Widlund et al. | |
| 5,354,400 | A * | 10/1994 | Lavash et al. | 156/227 |
| 5,374,260 | A * | 12/1994 | Lemay et al. | |
| 5,383,868 | A * | 1/1995 | Hyun | |
| 5,454,802 | A * | 10/1995 | Lindquist et al. | |
| 5,460,623 | A * | 10/1995 | Emenaker et al. | 604/368 |
| 5,545,156 | A | 8/1996 | DiPalma et al. | 604/385.1 |
| 5,558,656 | A | 9/1996 | Bergman | 604/385.1 |
| 5,569,231 | A * | 10/1996 | Emenaker et al. | 604/385.1 |
| 5,591,150 | A * | 1/1997 | Olsen et al. | 604/385.1 |
| H1634 | H * | 2/1997 | Oetjen et al. | 604/385.1 |
| 5,624,421 | A * | 4/1997 | Dabi et al. | 604/378 |
| 5,688,259 | A * | 11/1997 | Osborn, III et al. | 604/385.1 |
| 5,695,324 | A * | 12/1997 | Weirich | 604/378 |
| 5,704,931 | A * | 1/1998 | Holtman et al. | 604/387 |
| 5,722,967 | A * | 3/1998 | Coles | 604/385.1 |
| 5,741,241 | A | 4/1998 | Guidotti et al. | |
| 5,827,258 | A * | 10/1998 | McFall et al. | 604/385.1 |
| 5,849,003 | A * | 12/1998 | Olsen et al. | 604/387 |
| 5,853,401 | A * | 12/1998 | Mayer et al. | 604/378 |
| 5,873,869 | A * | 2/1999 | Hammons et al. | 604/385.1 |
| 5,919,178 | A | 7/1999 | Widlund | |
| 5,957,909 | A * | 9/1999 | Hammons et al. | 604/387 |
| 5,961,508 | A * | 10/1999 | Mayer et al. | 604/385.1 |
| 6,020,536 | A | 2/2000 | Osterdahl et al. | |
| 6,033,391 | A * | 3/2000 | Osborn, III et al. | 604/385.1 |
| 6,042,575 | A * | 3/2000 | Osborn, III et al. | 604/387 |
| 6,080,909 | A | 6/2000 | Osterdahl et al. | |
| 6,162,204 | A * | 12/2000 | Romare | 604/385.01 |
| 6,171,291 | B1 * | 1/2001 | Osborn, III et al. | 604/385.1 |
| 6,183,587 | B1 * | 2/2001 | McFall et al. | 156/201 |
| 6,191,340 | B1 * | 2/2001 | Carlucci et al. | 604/369 |
| 6,198,091 | B1 * | 3/2001 | Hansson et al. | 604/378 |
| 6,210,385 | B1 * | 4/2001 | Mizutani | 604/385.01 |
| 6,231,556 | B1 * | 5/2001 | Osborn, III | 604/385.1 |
| 6,293,931 | B1 * | 9/2001 | Romare | 604/385.01 |
| 6,293,935 | B1 * | 9/2001 | Kimura et al. | 604/387 |
| 6,296,628 | B1 * | 10/2001 | Mizutani | 604/387 |

FOREIGN PATENT DOCUMENTS

| | | | |
|---|---|---|---|
| EP | 0 235 763 A1 * | 9/1987 | |
| EP | 335 252 | 10/1989 | |
| EP | 335 253 | 10/1989 | |
| EP | 0 336 578 A1 * | 10/1989 | |
| EP | 339 041 B1 | 11/1991 | |
| EP | 0 606 082 A1 * | 7/1994 | |
| EP | 419 434 B2 | 11/1998 | |
| GB | 2 119 656 | 11/1983 | |
| GB | 2 119 657 | 11/1983 | |
| WO | 92/19197 | * 11/1992 | |
| WO | 93/15702 | * 8/1993 | |
| WO | 93/21879 | 11/1993 | |
| WO | 95/31165 | 11/1995 | |
| WO | 96/20679 | 7/1996 | |
| WO | 96/26699 | 9/1996 | |
| WO | 97/09015 | 3/1997 | |
| WO | 98/22058 | 5/1998 | |

OTHER PUBLICATIONS http://www.isobordenterprises.com; Isoboard Enterprises, Inc.; 2000.* http://www.stramit-int.com/panels.html; Stramit International, date unknown.* http://www.isobordenterprises.com/p_isobord.htm; Isoboard Enterprises, Inc.; 2000.* http://www.isobord.com/pr009.html; Isoboard Enterprises, Inc.; 1999.* http://www.strawboard.com; BioFab, LLC; Apr. 1997.* http://www.ricestraw.com/coffin; BioFab, LLC; 2000.*

* cited by examiner

ABSORBENT ARTICLE WITH A RAISED PORTION

TECHNICAL FIELD

The invention relates to an absorbent article, intended for female users, such as a sanitary napkin or an incontinence guard, with such a shape and size that it may be substantially accommodated in the crotch region of a pair of panties and having a longitudinal direction, a transverse direction and a thickness direction, wherein the article exhibits a liquid-pervious surface, and a liquid-impervious surface, and further an absorbent core consisting of at least one absorbent body arranged between the two surfaces, and wherein a hump is arranged at the liquid-pervious surface of the article.

BACKGROUND OF THE INVENTION

A common problem associated with absorbent articles of the herein intended type is leakage of body fluid past the longitudinal side edges of the article. Such leakage is of course extremely undesirable, since it entails the risk of soiling the clothing of the user. Because of the fairly insignificant extension of the article also in the longitudinal direction, it is furthermore not unusual that liquid leaks out forwards and backwards past the end edges of the article. Thereby, a particular problem is leakage backwards which usually arises in connection with the user lying down, for example during the night.

The most frequent reason for edge leakage is that the absorbent article is deformed during use, when the article is squeezed between the thighs of the user. In this way, wrinkling arises in an uncontrollable manner both in the absorbent core of the article and in its cover material.

Such wrinkling results in the formation of channels on the surface of the article, in which body fluid may seep out past the side edges. Furthermore, the compression of the article implies that the area accessible for liquid reception is reduced, whereby the risk of body fluid ending up beside the article is significant.

A further problem in connection with the previously known absorbent articles is that the side edges of the articles risk being folded in over the liquid-pervious surface of the article because of the action from the body forces which arise when the user moves about. The area accessible for liquid reception is also drastically reduced by such folding in, since only a narrow liquid-pervious region is thereby left between the inwardly-folded side edges.

One way of reducing the risk of edge leakage caused by deformation of the article during use is to provide the article with a pre-formed hump, which during use is intended to be in contact with the genitals of the user. Excreted body fluid may in this way be caught as soon as it leaves the body of the user and immediately be absorbed into the article without flowing out across the surface thereof.

Previously known absorbent articles provided with a liquid-receiving hump are, however, afflicted with a number of disadvantages.

A common way of creating a hump has been to simply build it up by arranging a larger amount of absorbent material within the area of the hump. Since the most commonly occuring absorbent material is so-called cellulose fluff pulp, such a hump, however, collapses and loses its shape when wetted. In order to achieve a hump which is sufficiently large also in a wet state, a hump consisting of cellulose fluff pulp must comprise so much absorbent material that it becomes far too high, hard and uncomfortable to wear in a dry state.

In order to solve the problem with large, hard and uncomfortable humps, it has been suggested in EP 0 339 041 that the liquid-impervious surface of the article be provided with transverse elastic members. Such elastic members impart a certain resiliency to the article if it is subjected to flattening. The elastic members, however, do not to any great extent prevent compression and undesired deformation in the transverse direction of the article.

In another publication, EP 0 419 434, it has been suggested to create a soft hump on an absorbent article by means of locking the side edges of the article at a mutual distance which is smaller than the planar distance between the side edges. Neither does this previously known article, to any appreciable extent, resist such deformation which is caused by the article being affected by pressure and shear forces during use.

In EP 0 335 252 and EP 0 335 253 it has been suggested to provide an absorbent article with a deformation element. The deformation element is affected by the transverse compressive forces between the thighs of a user. The purpose of the deformation element is that this during use should curve a portion of the article in a direction towards the body of the user. However, it is impossible to completely control, or anticipate the shape the article will adopt for each individual user. Furthermore, it is not possible to ensure the contact between the body of the user and the surface of the article, since the degree of bulging is completely determined by how much the article is compressed in a transverse direction.

Thus, there remains a need for a leakage-proof absorbent article, which has a predictable shape, both before and during use, and which maintains its shape independently of the movements of the user and of the wetting the article is subjected to.

An article designed according to the invention, of the type disclosed in the introduction, is primarily characterized in that the hump is substantially shape permanent in the transverse direction of the article both in a dry and in a wet state, and to such an extent that the hump is not deformed in the transverse direction, either temporarily or permanently, by the forces which act on the hump during use of the article.

Further variants and embodiments are evident from the following claims.

Since the article is provided with a hump which is shape permanent both in a wet and in a dry state, it is possible to predict the shape of the hump in every situation. The fact that the hump is shape permanent implies that it remains essentially unaffected in normal use and is not deformed when it is subjected to pressure and shear forces which arise in use. It is particularly important that the hump is not compressed in the transverse direction, between the thighs of the user. It is, however, in general also an advantage if the hump is substantially incompressible also in the thickness direction.

The height of the hump above the surface of the absorbent article must be adapted so that good contact between the body of the user and the hump is ensured during use. Since the hump is so hard or stiff that it is essentially unyielding to the forces it is subjected to during use it is, however, important that the hump is not so high that it presses against the body of the user and thereby causes discomfort during use. Furthermore, it is necessary to ensure that the hump does not chafe against the sensitive soft parts in the crotch of the user. Thereby, it has been found that a hump which at its highest part projects at least 5 mm from the surface of the article, but not more than 20 mm, fulfils the requirements both of good body contact and high user comfort.

A hump in accordance with the invention is relatively narrow, suitably between 2 mm and 25 mm at the base and preferably between 12 mm and 16 mm. At the top the hump is suitably between 3 mm and 10 mm wide and preferably between 4 mm and 6 mm. The hump is designed with a substantially triangular cross-section and is, consequently, wider at the base than at the top. Since the hump is comparatively narrow, it can protrude, without any discomfort to the user, slightly in between the labia pudendi of the user. Thereby, it is an advantage if the hump slightly separates the labia pudendi, since the liquid transfer from the user to the article is thus facilitated.

At the rear portion of the hump, it should have such a shape that it is in close contact with the body of the user, in the region behind the vaginal opening. Thereby, it is avoided that body fluid leaks backwards in the furrow between the buttocks of the user and leaks out from the article. As earlier mentioned, such leakage backwards is particularly embarrassing when the user is lying down. In a corresponding way, the front portion of the hump should conform to the body shape of the user in the region in front of the vaginal opening.

It is important that the body fluid which is emitted is immediately caught and absorbed into the hump. Liquid is thus prevented from collecting between the body of the user and the hump. When the user stands up or otherwise moves about, there is a risk that a gap will arise at the front portion of the hump, between the hump and the body of the user. If a large quantity of un-absorbed liquid has been trapped between the body of the user and the surface of the article, such liquid may then flow out through the gap. Such sudden liquid flows are extremely undesirable, partly because the user perceives them as unpleasant, and partly because they considerably increase the risk of leakage.

The length of the hump is furthermore of importance to the achievement of optimum contact between the hump and the body of the user. The hump should have such a shape and extend so far backwards on the article that it essentially seals against liquid flow backwards on the article. This is achieved by means of the hump being in sealing contact against the skin behind the vaginal opening of the user. A suitable length of the hump has thereby been found to be between 70 mm and 140 mm, preferably between 80 mm and 120 mm. The hump should not extend across the entire length of the article and, in particular, it is advantageuous if a portion at the front end of the article is free from the stiff, shape permanent hump. In this way, the front end may bend and conform to the curvature on the body of the user.

In order to conform to the anatomy of the user, the hump should be highest at the portion of the article which is intended to be in contact with the vaginal opening of the user. From the highest portion, the height should gradually decrease in a direction towards the end portions of the article. Thereby, the hump should extend backwards from the highest portion between 5 mm and 40 mm and preferably between 10 mm and 30 mm. In front of the highest portion, the hump should have a length of between 50 mm and 90 mm, preferably between 55 mm and 80 mm.

A raised edge barrier may advantageously be arranged at both sides of the central hump. The edge barriers increase the leakage-security of the article by serving as seals against the groin of the user. Raised edge barriers can be achieved in a number of different ways. Preferably, the edge barriers are made of the same material as the central hump and thereby have essentially the same resistance to deformation as the hump. However other types of edge barriers, such as elastic side edges, foam rubber strips, wadding, or the like, are conceivable. The edge barriers may either be purely physical barriers, or prevent liquid passage by means of absorbing body fluid.

SHORT DESCRIPTION OF THE DRAWINGS

The invention will in the following be described in greater detail with reference to the figures which are shown in the attached drawings.

DETAILED DESCRIPTION OF PREFERRED EMBODIMENTS

Figure 1:
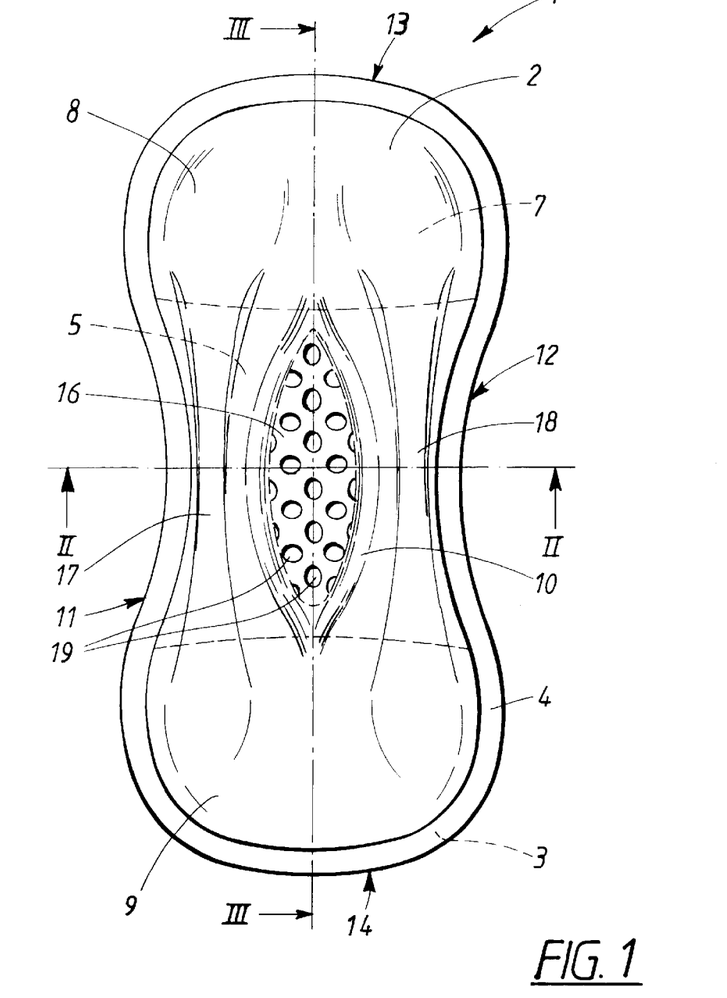
FIG. 1 shows a plan view of a sanitary napkin in accordance with the invention, seen from the side which in use is facing the user.
Figure 2:
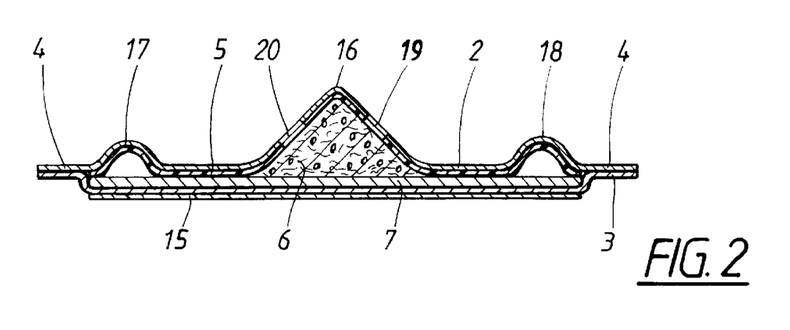
FIG. 2 shows a section along the line II—II through the sanitary napkin in FIG. 1.

The sanitary napkin 1 shown in FIGS. 1 and 2 comprises a liquid-pervious cover layer 2, arranged on the side of the sanitary napkin 1 which during use is intended to be facing the user. The liquid-pervious cover layer 2 suitably consists of soft, skin-friendly material. Examples of useful liquid-pervious cover materials are different types of non-woven fibre fabrics, so-called nonwoven materials. Other occurring liquid-pervious cover materials are perforated plastic films, scrims, knitted or woven fabrics, and combinations and laminates of the listed material types.

The sanitary napkin 1 further comprises a liquid-impervious cover layer 3, arranged at the side of the sanitary napkin 1 which during use is intended to be facing away from the user. Usually, a thin plastic film is used as a liquid-impervious cover layer 3. It is, however, also possible to use liquid-pervious material layers which are coated with a liquid-impervious material. Other treatments, such as thermo-calendering in order to fuse an originally liquid-pervious material into a substantially liquid-impervious layer, may also be utilized. It is furthermore possible to use nonwoven materials, or other textiles which are sufficiently dense and the fibres of which are sufficiently hydrophobic that they may function as a liquid barrier layer.

The two cover layers 2, 3 are mutually interconnected and form a protruding connecting edge 4 around the periphery of the sanitary napkin. The connection between the cover layers 2, 3 may be achieved by means of any previously known technique suitable for the purpose, such as gluing, welding or sewing.

Between the cover layers 2, 3, in a direction from the liquid-pervious cover layer 2 towards the liquid-impervious cover layer 3, there is a shape-retaining element 5, a first absorbent body 6, and a second absorbent body 7.

The sanitary napkin 1 is hourglass-shaped, with relatively wider front portion 8 and rear portion 9, and with a narrower intermediate crotch portion 10. The sanitary napkin 1 furthermore exhibits two longitudinal concavely-curved side edges 11, 12, and also two convexly-curved end edges 13, 14.

An attachment member 15, in the form of a longitudinal rectangular region of self-adhesive glue, is arranged on the surface of the liquid-impervious cover layer 3 which is turned away from the user. The attachment member 15 extends across the greater part of the surface of the liquid-impervious cover layer 3, between the two end edges 13, 14. It is of course possible to use other glue patterns, such as longitudinal stripes, transverse regions, dots, circles, or other designs. Moreover, the invention is not limited to adhesive attachment members, but frictional attachment devices such as snap fasteners, clips, girdles, pants, or the like may be utilized where suitable. The extension and location of the shape-retaining element 5, corresponds on the whole, to the shape and the dimension of the crotch portion 10 of the sanitary napkin 1. The shape-retaining element 5 has a predetermined, three-dimensional shape with a central hump 16, extending in the longitudinal direction of the sanitary napkin, and two raised edge barriers 17, 18, arranged along the side edges 11, 12 of the sanitary napkin 1, on each side of the central hump. The central hump 16 and the edge barriers 17, 18 project from the plane of the sanitary napkin on the side of the sanitary napkin which during use is intended to be facing the user. Thereby, the intention is that the central hump 16 should be in contact against the body of the user and be partly inserted between the outer labia pudendi of the user. The edge barriers 17, 18 are situated in the groin of the user during use and seal against leakage past the side edges 11, 12 of the sanitary napkin.

The central hump 16 has an elongated shape and tapers in a direction towards the end portions 8, 9 of the sanitary napkin 1. Thereby, the hump is highest at the region which during use is intended to be in contact with the vaginal opening of the user. The length of the hump is suitably approximately 115 mm, but may if desired vary between 70 mm and 140 mm. Thereby, the hump suitably extends approx. 20 mm backwards from the highest portion and approx. 75 mm forwards from the highest portion. Also these measures may, however, be varied within the above-mentioned limits.

Within the region of the hump 16, both the shape-retaining element 5 and the liquid-pervious cover layer 2 are provided with a plurality of apertures 19, or perforations, which allow liquid passage into the first absorbent body 6, situated in the shape-retaining element 5 inside the hump 16. When using such a perforated shape-retaining element, the liquid-pervious cover layer 2 may be omitted, at least within the region of the hump 16. Generally, however, for reasons of comfort it is desirable to cover the stiff, hard shape element with a softer material.

The shape-retaining element 5 is designed in a shape permanent, stiff sheet material such as hard plastic, stiff paper, cardboard, a stiff nonwoven material, laminate, or the like. It is essential for the invention that the shape-retaining element 5, at least in the transverse direction, is sufficiently shape permanent that the central hump 16 during use substantially resists the compression forces from the thighs of the user, without being either temporarily or permanently deformed. It is suitable, but not necessary, that the central hump 16 also resists compression in the thickness direction. The degree of deformability of the central hump 16 in the thickness direction is decided by the material stiffness of the shape-retaining element 5 in combination with the number of apertures 19 in the hump 16, and also the size of the apertures 19. At the same basic stiffness of the material in the shape-retaining element 5, the deformability increases with the number of apertures 19 as well as with the size of the apertures 19. Furthermore, the stiffness of the hump 16 is influenced by the stiffness of the absorbent material which is arranged inside the hump.

The first absorbent body 6, arranged inside the shape-retaining element 5, is situated inside the central hump 16. Due to the shape of the sanitary napkin, with the central hump 16, the sanitary napkin is maintained in contact with the body of the user during use. The fluid which is emitted is therefore immediately caught by the hump 16 and passes through the apertures 19 in the shape-retaining element 5 into the first absorbent body 6. Since the first absorbent body 6 is intended to receive and absorb almost all emitted body fluid, the absorption capacity of the first absorbent body should correspond to the total liquid amount which the sanitary napkin is estimated to absorb during use.

Figure 3:
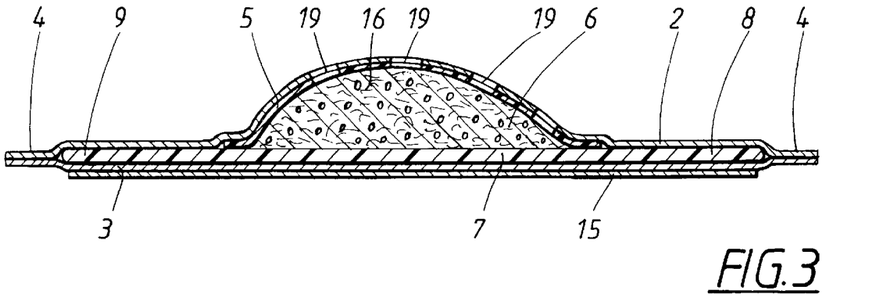
FIG. 3 shows a longitudinal section along the line III—III through the sanitary napkin in FIG. 1.

In the cross-sectional FIGS. 2 and 3, the first absorbent body 6 is shown as a fibre wadding containing particles of super-absorbent material, evenly distributed in the fibre structure. Super-absorbent material refers to polymers which are available in the form of fibres, flakes, particles, granules, or the like and which are able to absorb several times their own weight of body fluid during swelling and forming of a gel. A particular advantage with the use of super-absorbent material in connection with the sanitary napkin shown in FIGS. 1–3, is that the space available for absorbent material in the central hump 16 is fairly limited. By utilizing super-absorbent material, it is possible to build in a large absorption capacity, even in the comparatively small space beneath the central hump 16 in the shape-retaining element 5.

Other suitable absorbent materials for use in the first absorbent body 6 are for example cellulose fluff pulp, cotton, absorbent foam material, or the like.

For maximum utilization of the absorption capacity of the absorbent material, it is necessary to ensure that there is sufficient space for expansion during absorption. By using a liquid-impervious cover layer 3, which has a certain flexibility and elasticity, the super-absorbent material may expand both so that it fills up the central hump, and, by stretching the liquid-impervious cover layer 3, so that a bulge is formed on the side of the sanitary napkin 1 which is facing away from the user.

The absorbent material in the first absorbent body 6 may further consist of a mixture of absorbent and non-absorbent material. An example of such a mixture is a non-absorbent fibre structure with bonded super-absorbent fibres or particles.

A type of absorbent material which has been found to be particularly suitable for use in the first absorbent body, are those fibre materials which are described in WO 94/10953 and WO 94/10956. Since the shape-retaining element 5 prevents the absorbent material from swelling in a direction towards the body of the user, the hump 16 maintains its shape against the user during use. However, it is possible to use material which swells when it absorbs liquid. The first absorbent body may thereby be allowed to expand in a direction away from the body of the user, since the liquid-impervious cover layer 3 is resilient and admits such expansion.

The second absorbent body 7 is arranged between the first absorbent body 6 and the liquid-impervious cover layer 3. The second absorbent body 7 has a fairly limited absorption capacity in comparison with the first absorbent body 6. Due to this, the second absorbent body 7 primarily serves as a reserve which is made use of for absorption when the first absorbent body 6 has been saturated with liquid. The second absorbent body 7 also has the ability to absorb a minor amount of liquid such as perspiration or occasional droplets which may happen to trickle out to the end portions 8, 9 of the sanitary napkin 1. Furthermore, the second absorbent body 7 increases the stability in the soft, pliable end portions 8, 9, and makes the sanitary napkin softer against the body of the user.

The absorbent material in the second absorbent body 7 is suitably constituted by one, or several, layers of a conventional absorbent material. Examples of useful materials are tissue layers, wadding layers of synthetic or natural fibres, layers of cellulose fluff pulp, absorbent foam layers, or the like.

In the sanitary napkin 1, in FIGS. 1–3, the good contact between the hump 16 and the body of the user ensures that substantially no body fluid flows out towards the sides from the hump 16. If, in spite of this, a small quantity of body fluid should pass out towards the side edges of the sanitary napkin, leakage is efficiently prevented by means of the raised edge barriers 17, 18. The edge barriers 17, 18 conduct the liquid forwards, or backwards to the edge portions 8, 9 of the sanitary napkin, where it may enter through the liquid-pervious cover layer 2 into the second absorbent body 7, situated on the inside. If found to be desirable, it is of course possible to arrange a small quantity of absorbent material inside the liquid-pervious cover layer 2, between the edge barriers 17, 18 and the central hump 16, in order to prevent liquid from flowing on the surface of the sanitary napkin.

Figure 4:
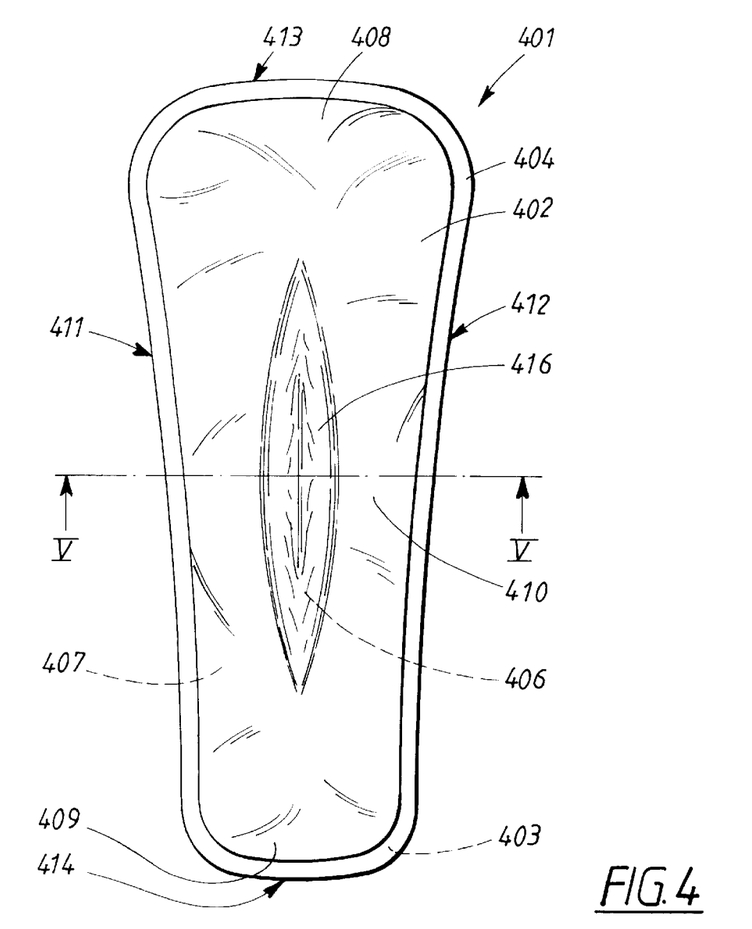
FIG. 4 shows a plan view of a sanitary napkin according to a second embodiment of the invention, seen from the side which in use is facing the user.
Figure 5:
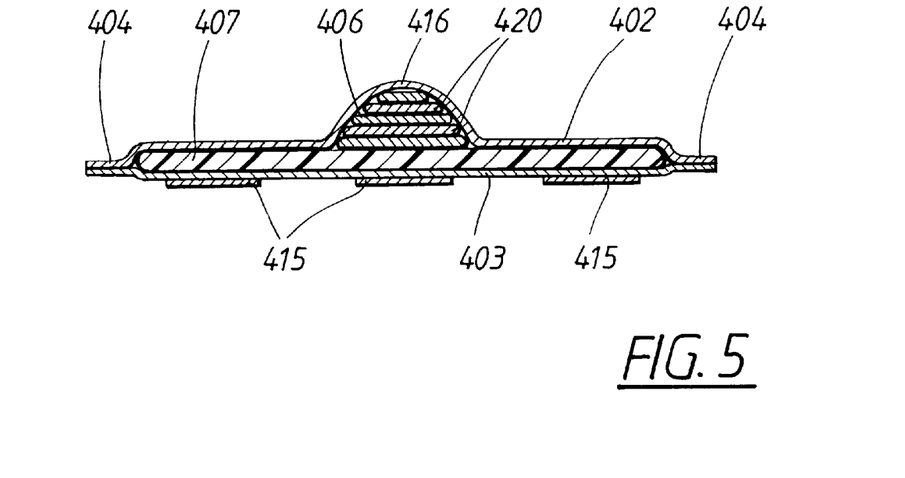
FIG. 5 shows a cross-section along the line V—V through the sanitary napkin FIG. 4.

The sanitary napkin 401, shown in FIGS. 4 and 5, has the same general structure as the sanitary napkin 1, shown in FIGS. 1–3. However, the sanitary napkin 401 in FIGS. 4 and 5 lacks a special shape-retaining element. Accordingly, the sanitary napkin 401 comprises a liquid-pervious cover layer 402, a liquid-impervious cover layer 403, and a first absorbent body 406 and a second absorbent body 407, enclosed between the cover layers 402, 403. The cover layers 402, 403 are mutually interconnected around the absorbent bodies 406, 407 and thereby form a connecting edge 404 around the periphery of the sanitary napkin 401.

The sanitary napkin 401 has a trapezium shape, with a wider front portion 408, a narrower rear portion 409, and an intermediate centre portion 410. Furthermore, the sanitary napkin 401 has two oblique side edges 411, 412, which extend between two almost straight end edges 413, 414.

An adhesive attachment member 415 is arranged in the form of three glue lines, travelling in the longitudinal direction of the sanitary napkin 401, on the liquid-impervious cover layer 403.

An elongated hump 416 is arranged centrally in the longitudinal direction of the sanitary napkin 401. The hump 416 is widest at the centre portion 410 of the sanitary napkin and tapers in a direction towards the front and the rear portions 408, 409. Furthermore, it is suitable that the hump 416 is profiled in the longitudinal direction, so that it is highest at the centre portion 410 and gradually decreases in height in a direction towards the end portions 408, 409.

The hump 416 is constituted by a plurality of willowleaf-shaped layers 420 of a highly absorbent fibre material. The willowleaf-shaped layers 420 together constitute the first absorbent body 406 of the sanitary napkin 401, which consequently constitutes the hump 416.

Figure 6:
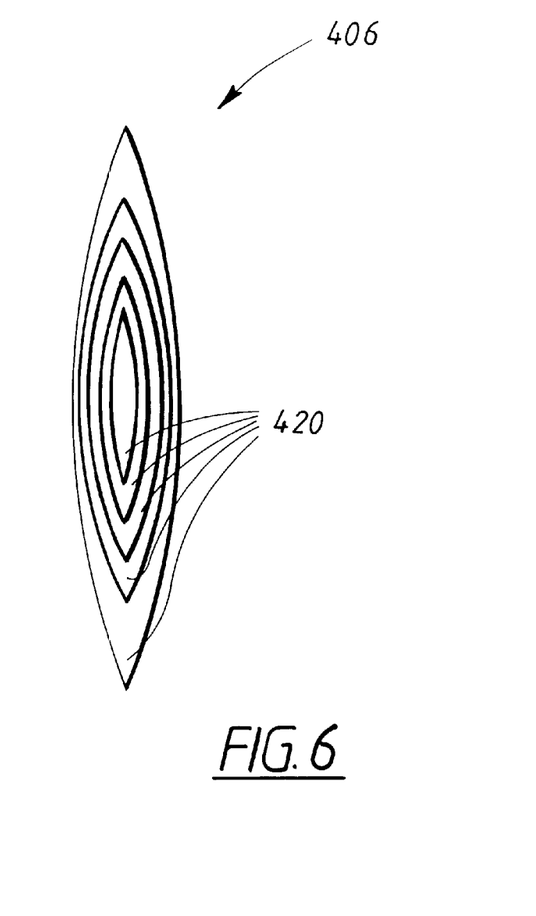
FIG. 6 shows a portion of the absorbent core in the sanitary napkin of FIG. 4 seen from the side which in use is facing the user.

FIG. 6 shows the first absorbent body 406. The absorbent body 406 is seen from the side which during use is facing the user. In order to obtain the desired ridge-like shape of the absorbent body 406, the integral layers 420 of absorbent material have been stacked on each other. Thereby, the layer 420, which in FIG. 6 is situated furthest away from the viewer, has the largest extension, whereafter the layers 420 diminish in area in a direction towards the viewer. The layers 420 are nearly congruent and are arranged concentrically in relation to each other. As a consequence, the first absorbent body 406 is imparted a stepped cross-sectional profile.

A shape of a similar kind is achieved by arranging the layers 420 in reversed order, with the smallest layer at the bottom and gradually increasing layer dimensions in a direction towards the top of the hump. In such an arrangement, the larger layers are draped over the smaller layers, so that the final result is a hump which tapers towards the top.

Another way of achieving an absorbent body 406 with a suitable shape, is by rolling together a triangular blank of an absorbent material. The blank has the shape of an isosceles triangle and is rolled together from the base towards the corner between the two edges having equal length. By means of this method, the resulting absorbent body becomes spool-shaped, with a thicker centre portion and narrower end portions.

A further way of achieving an absorbent body having the desired shape is by placing a number of plates, or material layers, of an absorbent material on end. By choosing a suitable absorbent material it is thereby possible to achieve an absorbent body with a very good shape permanence both in a transverse and in a vertical direction.

A suitable material for the absorbent body shown in FIG. 6 is the absorbent material which is disclosed in WO 94/10956. This material is a dry-formed fibre layer with high density and stiffness, which is used directly in an absorbent article, without first being defibered. Another similar material, with particularly suitable properties for blood-absorption purposes,, is disclosed in WO 94/10953. The materials disclosed in WO 94/10956 and 94/10953 both have sufficient stiffness and ability to resist pressure deformation, in order to provide the central hump 416 on the sanitary napkin 401 in FIG. 4 with the desired shape stability. Furthermore, these fibre materials have a very good absorption capacity. During absorption the material swells slightly in the thickness direction and in this way conforms to the available space in the crotch of the user. An advantage with this is that the hump 416 during use adopts a shape which is uniquely adapted to each respective user. In this way, both the leakage security and the user comfort are increased.

The second absorbent body 407 of the sanitary napkin 401 is located between the first absorbent body 406 and the liquid-impervious cover layer 403. The second absorbent body 407 primarily constitutes a protection against edge leakage around the central hump 416. Secondly, it also serves as an additional absorption capacity which can be made use of if the first absorbent body 406 is saturated by unexpectedly large liquid quantities. Furthermore, the second absorbent body 407 is responsible for providing the sanitary napkin 401 with an extension length in the plane, so that the sanitary napkin 401 may be attached inside a pair of panties by means of the attachment member 415 arranged on the liquid-impervious cover layer 403.

Figure 7:
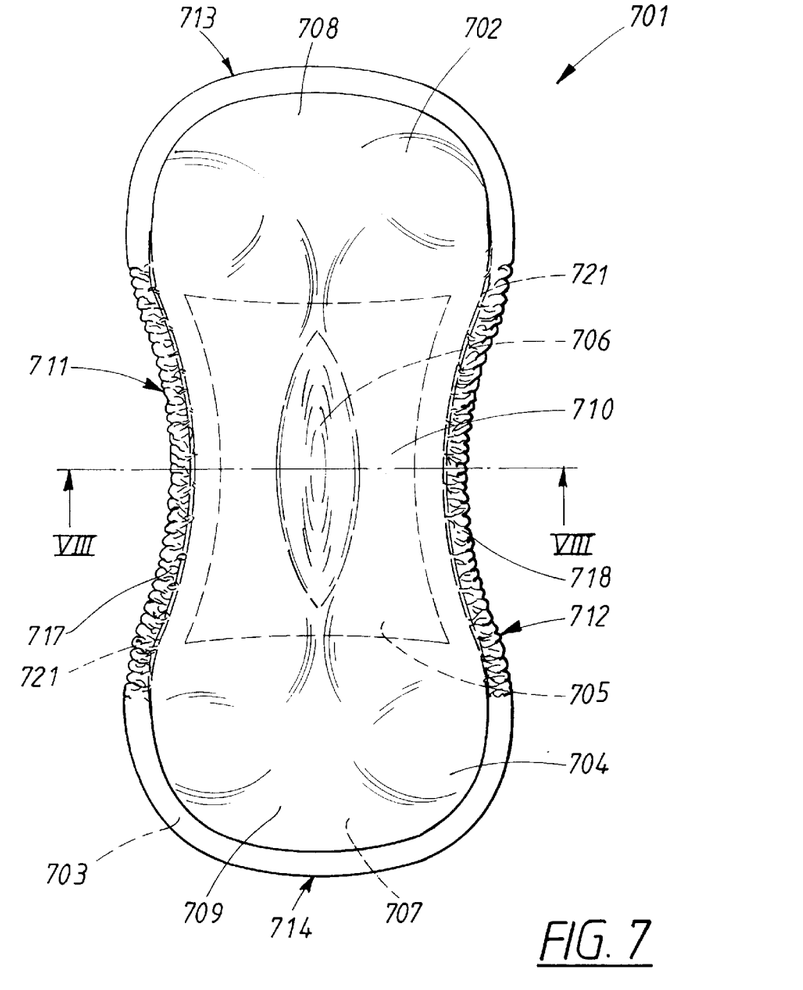
FIG. 7 shows a sanitary napkin according to a third embodiment of the invention, seen from the side which in use is facing the user

The sanitary napkin 701, shown in FIG. 7, comprises a liquid-pervious cover layer 702, a liquid-impervious cover layer 703, which are mutually interconnected within a connection edge 704 around the periphery 701 of the sanitary napkin 701.

The sanitary napkin 701 is hourglass-shaped, with two end portions 708, 709 and a narrower centre portion 710. Furthermore, the sanitary napkin 701 exhibits two longitudinal side edges 711, 712 and two transverse end edges 713, 714.

Figure 8:
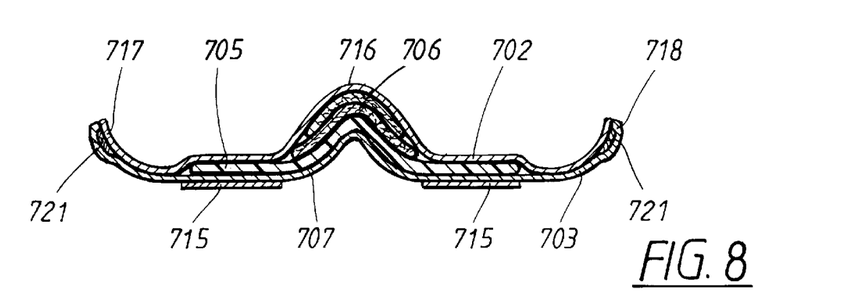
FIG. 8 shows a cross-section along the line VII—VII through the sanitary napkin in FIG. 7.

A shape-providing material layer 707, having substantially the same shape and dimensions as the sanitary napkin 701 as a whole, is arranged between the two cover layers 702, 703. The material layer 707 is substantially non-absorbent, soft and resilient. The main purpose of the material layer 707 is to provide the sanitary napkin 701 with the shown hourglass-shape. Since the material layer 707 has a certain resiliency, both in the thickness direction and in the plane of the layer, the material layer 707 also provides user comfort and shape permanence in the sanitary napkin 701.

A shape-retaining element 705, of the kind which is shown in FIGS. 1–3, is arranged at the centre portion 710 of the sanitary napkin 701. Accordingly, the shape-retaining element 705 is made from a material which is so stiff that it essentially completely resists compression during use. The shape-retaining element 705 is not deformable, either in the cross direction or in the thickness direction, when it is subjected to the body forces which arise during normal use.

The shape-retaining element 705 is constituted by an almost rectangular material piece, which in the transverse direction of the sanitary napkin ends a distance inside of the side edges 711, 712 of the sanitary napkin 701. In the longitudinal direction of the sanitary napkin, the shape-retaining element 705 extends only across the centre portion 710. A longitudinal, ridge-like hump 716, is formed centrally on the shape-retaining element 705. The hump 716 is lower closest to the end portions 708, 709 than at the central part of the centre portion 710.

An absorbent body 706, consisting of one or several layers of absorbent material is arranged over the hump 716, between this and the liquid-pervious cover layer 702. The absorbent material may be selected in the same way as the absorbent material in the humps 16, 416, described in connection with FIGS. 1–6.

Raised edge barriers 717, 718 are arranged along the side edges 711, 712 of the sanitary napkin 701. The edge barriers 717, 718 are formed by means of elastic members 721 being attached in a stretched condition between the two cover layers 702, 703, along the side edges 711, 712 at the centre portion 710 of the sanitary napkin. The elastic members 721 may be of any conventional kind, such as elastic bands, threads, elastic nonwoven material, or the like. The elastic members 721 may of course optionally be attached to the outside of one of the cover layers 702, 703, or be constituted by a band of an elastic foam material, elastic nonwoven material, or the like, which has been folded around the connection edge 704 formed by the cover layers 702, 703. A number of different ways of attaching elastic members 721 to one or two material layers are previously known, and may be used in order to achieve the raised edge barriers 717, 718.

The sanitary napkin is furthermore, in a conventional way, provided with attachment members 715, in the form of two longitudinal stripes of self-adhesive, pressure-sensitive glue.

The invention has in the foregoing been described in connection with sanitary napkins. However, it is possible to utilize the invention also for other absorbent articles which are intended to be worn by female users. Accordingly, the invention also embraces panty-liners and incontinence guards for women.

The invention should not be regarded as being limited to the herein described embodiments, but a number of further variants and modifications are conceivable within the scope of the claims. Furthermore, all conceivable combinations of the described embodiments are intended to be embraced by the invention.

What is claimed is:

1. An absorbent article intended for female users, with such a shape and size that it may be substantially accommodated in the crotch region of a pair of panties and having a longitudinal direction, a transverse direction and a thickness direction, comprising:

a liquid-pervious cover layer;

a liquid-impervious cover layer;

an absorbent core consisting of at least one absorbent body, arranged between the two cover layers; and a single centrally arranged hump arranged at the liquid-pervious cover layer of the article, wherein the hump is substantially shape permanent in the transverse direction of the article, both in a wet and in a dry state, and to such an extent that the hump is not deformed in the transverse direction, either temporarily or permanently, by the forces which act upon the hump during use of the article, wherein the hump projects from a plane of the side of the article having the liquid-pervious cover layer, and wherein the hump has a base, facing the liquid-impervious cover layer, and a top, facing the liquid-pervious cover layer, whereby the extension of the hump in the transverse direction of the article is between 2 mm and 25 mm at the base, and the extension of the hump in the transverse direction at the top is between 3 mm and 10 mm, and the hump is wider at the base than at the top.

2. An article according to claim 1, wherein the hump is substantially shape permanent in the thickness direction of the article, whereby the article will not be permanently deformed by the pressure forces, acting in the thickness direction of the article, which arise during normal use of the article.

3. An article according to claim 1, further comprising a shape retaining element, wherein the hump is formed by the shape-retaining element.

4. An article according to claim 3, wherein the shape-retaining element comprises a layer of stiff plastic material.

5. An article according to claim 3, wherein at least a first absorbent body is arranged inside the shape-retaining element, seen in a direction from the liquid-pervious surface of the article, and that the shape-retaining element exhibits at least one through-going aperture, within the region of the hump, through which body fluid may pass into the first absorbent body.

6. An article according to claim 3, wherein an absorbent body is arranged between the shape-retaining element and the liquid-pervious cover layer of the article.

7. An article according to claim 1, wherein the hump is between 70 mm and 140 mm in the longitudinal directions of the article.

8. An article according to claim 1, wherein the hump is between 80 mm and 120 mm in the longitudinal direction of the article.

9. An article according to claim 1, wherein the hump has a base, facing the liquid-impervious cover layer, and a top, facing the liquid-pervious cover layer, whereby the extension of the hump in the transverse direction of the article is between 12 mm and 16 mm at the base, and the extension of the hump in the transverse direction at the top is between 4 mm and 6 mm, and the hump is wider at the base than at the top.

10. An article according to claim 1, wherein the liquid-pervious cover layer conforms to the hump and has substantially the same shape as the hump where the liquid-pervious cover layer covers the hump.

11. An absorbent article according to claim 1, wherein the absorbent article is a sanitary napkin or incontinence guard.

12. An absorbent article intended for female users, with such a shape and size that it may be substantially accommodated in the crotch region of a pair of panties and having a longitudinal direction, a transverse direction and a thickness direction, comprising:

a liquid-pervious cover layer;

a liquid-impervious cover layer;

an absorbent core comprising at least one absorbent body, arranged between the two cover layers; and a single centrally arranged hump arranged at the liquid-pervious cover layer of the article, wherein the hump is substantially shape permanent in the transverse direction of the article, both in a wet and in a dry state, and to such an extent that the hump is not deformed in the transverse direction, either temporarily or permanently, by the forces which act upon the hump during use of the article, wherein the hump projects from a plane of the side of the article having the liquid-pervious cover layer, and wherein the hump has a base, facing the liquid-impervious cover layer, and a top, facing the liquid-pervious cover layer, whereby the extension of the hump in the transverse direction of the article is between 2 mm and 25 mm at the base, and the extension of the hump in the transverse direction at the top is between 3 mm and 10 mm, and the hump is wider at the base than at the top, and the absorbent article including two longitudinal side edges, wherein raised edge barriers are arranged along the longitudinal side edges.

13. An article according to claim 3, wherein the edge barriers are formed by the arrangement of pre-tensioned elastic members mounted along the side edges.

14. An absorbent article according to claim 12, wherein the absorbent article is a sanitary napkin or incontinence guard.

15. An absorbent article, intended for female users, such as a sanitary napkin, or an incontinence guard, with such a shape and size that it may be substantially accommodated in the crotch region of a pair of panties and having a longitudinal direction, a transverse direction and a thickness direction, comprising:

a liquid-pervious cover layer;

a liquid-impervious cover layer;

an absorbent core comprising at least one absorbent body, arranged between the two cover layers; and a single centrally arranged hump arranged at the liquid-pervious cover layer of the article, wherein the hump is substantially shape permanent in the transverse direction of the article, both in a wet and in a dry state, and to such an extent that the hump is not deformed in the transverse direction, either temporarily or permanently, by the forces which act upon the hump during use of the article, wherein the hump projects from a plane of the side of the article having the liquid-pervious cover layer, and wherein the hump has a base, facing the liquid-impervious cover layer, and a top, facing the liquid-pervious cover layer, whereby the extension of the hump in the transverse direction of the article is between 2 mm and 25 mm at the base, and the extension of the hump in the transverse direction at the top is between 3 mm and 10 mm, and the hump is wider at the base than at the top;

the absorbent article further comprising a shape-retaining element, wherein the hump is formed by the shape-retaining element; and wherein edge barriers are formed by the shape-retaining element.

16. An absorbent article intended for female users with such a shape and size that it may be substantially accommodated in the crotch region of a pair of panties and having a longitudinal direction, a transverse direction and a thickness direction, the absorbent article comprising:

a liquid-pervious cover layer;

a liquid-impervious cover layer;

an absorbent core comprising at least one absorbent body arranged between the two cover layers; and a centrally arranged hump extending from the absorbent core toward the liquid-pervious cover layer of the article, wherein the hump is substantially shape permanent in the transverse direction of the article, both in a wet and in a dry state, and to such an extent that the hump is not deformed in the transverse direction, either temporarily or permanently, by the forces which act upon the hump during use of the article; and wherein the liquid-pervious cover layer conforms to the hump and has substantially a same shape as the hump where the liquid-pervious cover layer covers the hump.

17. An absorbent article according to claim 16, wherein the hump comprises a body of absorbent material.

18. An absorbent article according to claim 17, wherein the hump further comprises a shape-retaining element arranged between the body of absorbent material and the liquid-permeable cover layer.

19. An absorbent article according to claim 16, wherein the liquid-permeable cover layer comprises a perforated shape-retaining element.

20. An absorbent article according to claim 16, wherein the hump comprises a body of absorbent material between the one absorbent body and the liquid-permeable cover layer.

* * * * *